(12) United States Patent
Ghelli et al.

(10) Patent No.: US 7,238,320 B2
(45) Date of Patent: Jul. 3, 2007

(54) DEVICE FOR OXYGENATING BLOOD IN AN EXTRACORPOREAL CIRCUIT

(75) Inventors: Nicola Ghelli, Casale (IT); Edgardo Costa Maianti, Mirandola (IT); Ivo Panzani, Mirandola (IT)

(73) Assignee: Sorin Group Italia S.r.l., Mirandola (IT)

( * ) Notice: Subject to any disclaimer, the term of this patent is extended or adjusted under 35 U.S.C. 154(b) by 382 days.

(21) Appl. No.: 10/804,929

(22) Filed: Mar. 19, 2004

(65) Prior Publication Data

US 2004/0175292 A1 Sep. 9, 2004

Related U.S. Application Data

(62) Division of application No. 09/920,999, filed on Aug. 2, 2001, now Pat. No. 6,723,283.

(30) Foreign Application Priority Data

Aug. 8, 2000 (IT) ............................ MI2000A1852

(51) Int. Cl.
*A61M 1/00* (2006.01)
*A61M 37/00* (2006.01)
(52) U.S. Cl. ...................... 422/45; 604/4.01; 604/6.14; 128/DIG. 3; 261/DIG. 28; 261/5; 261/6; 261/158; 261/24; 435/289.1; 435/297.1
(58) Field of Classification Search ............ 422/44–48; 604/4.01, 6.14; 128/DIG. 3; 261/DIG. 28, 261/1, 2, 5, 6, 158, 19, 20, 24, 28, 29, 75, 261/100–110; 435/283.1, 289.1, 297.1–297.2, 435/294.1
See application file for complete search history.

(56) References Cited

U.S. PATENT DOCUMENTS 2,319,730 A 5/1943 Garraway
2,659,368 A 11/1953 Gibbon, Jr. et al.

(Continued)

FOREIGN PATENT DOCUMENTS

EP 0 724 889 A2 8/1996

(Continued)

OTHER PUBLICATIONS

European Search Report for Application No. 03015535.2 (3 pages).

*Primary Examiner*—Tatyana Zalukaeva
(74) *Attorney, Agent, or Firm*—Popovich, Wiles & O'Connell, P.A.

(57) ABSTRACT

A device for oxygenating blood in an extracorporeal circuit includes a first structure suitable to delimit a portion of space-containing capillaries made of microporous membrane. The capillaries convey oxygen and are wet externally by blood flowing through a portion of space between an intake connector, which is connected to a venous line of the extracorporeal circuit, and a delivery connector. The device includes a second structure monolithically connected and contiguous to the first structure. The second structure is suitable to contain blood filtration means that divide the portion of space delimited thereby into a blood distribution chamber, provided with an air vent and connected to the delivery connector of the first structure, and a blood collection chamber provided with a delivery connector connected to the arterial line of the extracorporeal circuit.

5 Claims, 7 Drawing Sheets

U.S. PATENT DOCUMENTS

| | | | |
|---|---|---|---|
| 4,490,331 A | 12/1984 | Steg, Jr. | |
| 4,540,399 A | 9/1985 | Litzie et al. | |
| 4,610,656 A | 9/1986 | Mortensen | |
| 4,676,771 A | 6/1987 | Henke | |
| 4,698,207 A | 10/1987 | Bringham et al. | |
| 4,876,066 A | 10/1989 | Bringham et al. | |
| 5,039,482 A | 8/1991 | Panzani et al. | |
| 5,266,265 A | 11/1993 | Raible | |
| 5,308,320 A | 5/1994 | Safar et al. | |
| 5,312,479 A | 5/1994 | Weinstein et al. | |
| H001324 H | 6/1994 | Dalke et al. | |
| 5,391,142 A | 2/1995 | Sites et al. | |
| 5,411,705 A | 5/1995 | Thor et al. | |
| 5,573,526 A | 11/1996 | Hess | |
| 5,582,794 A | 12/1996 | Hagiwara et al. | |
| 5,632,894 A | 5/1997 | White et al. | |
| 5,728,069 A | 3/1998 | Montevecchi et al. | |
| 5,762,869 A | 6/1998 | White et al. | |
| 5,770,149 A * | 6/1998 | Raible | 422/46 |
| 5,782,791 A | 7/1998 | Peterson et al. | |
| 5,817,278 A | 10/1998 | Fini et al. | |
| 5,924,848 A | 7/1999 | Izraelev | |
| 5,958,338 A | 9/1999 | Lindsay et al. | |
| 6,059,111 A | 5/2000 | Davila et al. | |
| 6,162,017 A | 12/2000 | Raible | |
| 6,306,346 B1 | 10/2001 | Lindsay | |
| 6,311,838 B1 | 11/2001 | Johnson et al. | |
| 6,428,747 B1 | 8/2002 | Dueri et al. | |
| 6,451,257 B1 | 9/2002 | Flamer | |
| 6,468,473 B1 | 10/2002 | Lindsay | |
| 6,689,315 B2 | 2/2004 | Linker et al. | |
| 6,723,283 B2 | 4/2004 | Ghelli et al. | |
| 6,773,426 B2 | 8/2004 | Tamari | |
| 6,852,280 B2 | 2/2005 | Vijay et al. | |
| 2001/0010802 A1 | 8/2001 | Tamari | |
| 2002/0049401 A1 | 4/2002 | Ghelli et al. | |
| 2002/0085952 A1 | 7/2002 | Ellingboe et al. | |
| 2003/0163078 A1 | 8/2003 | Fallen et al. | |
| 2004/0054316 A1 | 3/2004 | Maianti et al. | |
| 2004/0219060 A1 | 11/2004 | Maianti et al. | |
| 2004/0223873 A1 | 11/2004 | Maianti et al. | |

FOREIGN PATENT DOCUMENTS

| | | |
|---|---|---|
| EP | 0 724 889 A3 | 9/1997 |
| EP | 0 987 035 A2 | 3/2000 |
| EP | 0 987 035 A3 | 3/2000 |
| EP | 1 180 374 A1 | 2/2002 |

* cited by examiner

Fig. 8 ated and contiguous to the first structure suitable to contain blood filtration means which divide the portion of space delimited thereby into a blood distribution chamber, provided with an air vent and connected to the delivery connector of the first structure, and a blood collection chamber which is provided with a delivery connector which is connected to the arterial line of the extracorporeal circuit.
DEVICE FOR OXYGENATING BLOOD IN AN EXTRACORPOREAL CIRCUIT

CROSS-REFERENCE TO RELATED APPLICATION

This Application is a divisional of application Ser. No. 09/920,999, filed Aug. 2, 2001, now U.S. Pat. No. 6,723,283 B2, hereby incorporated herein by reference.

FIELD OF THE INVENTION

This invention relates to a device for oxygenating blood in an extracorporeal circuit.

BACKGROUND OF THE INVENTION

During surgery, blood flows through extracorporeal circuits. The extracorporeal circuits include an oxygenation device to transfer oxygen to the blood received from the patient by means of a line which is known as venous line and then return it to the patient by means of a line known as arterial line.

The structure of the oxygenator is such as to delimit a portion of space which contains capillaries made of microporous membrane which convey oxygen and are wet externally by the blood that flows through this portion of space. There are also oxygenators which include a heat exchanger through which the blood is meant to flow before entering the oxygenator in order to be kept at the correct temperature.

Often on the arterial line there is a filter (the arterial filter), which is meant to retain any air bubbles present in the blood in order to prevent them from remaining in the blood that returns to the patient. However, this presence can be the source of problems for operators when one considers the inherent complexity of the extracorporeal circuit in which the arterial filter is introduced.

SUMMARY OF THE INVENTION

The aim of the present invention is therefore to provide a blood oxygenation device in which the extracorporeal circuit is simplified and which offers maximum safety in preventing air bubbles from being contained in the blood that returns to the patient.

The proposed aim is achieved by a blood oxygenation device comprising a first structure suitable to delimit a portion of space which contains capillaries made of microporous membrane. The capillaries convey oxygen and are wet externally by blood flowing through the portion of space between an intake connector, which is connected to the venous line of the extracorporeal circuit, and a delivery connector. There is a second structure monolithically connected and contiguous to the first structure suitable to contain blood filtration means which divide the portion of space delimited thereby into a blood distribution chamber, provided with an air vent and connected to the delivery connector of the first structure, and a blood collection chamber which is provided with a delivery connector which is connected to the arterial line of the extracorporeal circuit.

In one aspect, this invention is a device for oxygenating and filtering blood in an extracorporeal circuit comprising a housing defining first and second interior chambers, the first chamber containing a plurality of microporous filters and having a blood inlet and a blood outlet connected to the first chamber to define a blood flow path along an exterior of the hollow fibers and having a gas inlet and a gas outlet connected to the first chamber to define a gas flow path through the lumens of the hollow fibers, the second chamber containing a filtration membrane and having a blood inlet and a blood outlet connected to the second chamber to define a blood flow path through the filtration membrane, the blood inlet of the second chamber being connected to receive blood from the blood outlet of the first chamber.

In a second aspect, this invention is an integrated device for oxygenating and filtering blood in an extracorporeal circuit, comprising an oxygenator having a housing including a top, a bottom, and a side wall together defining an oxygenation chamber containing a microporous membrane, the housing having a blood inlet and a blood outlet positioned to define a blood flow path along a first side of the microporous membrane and a gas inlet and a gas outlet positioned to define a gas flow path along a second side of the microporous membrane; and an arterial blood filter having a housing including a top and bottom, a substantially cylindrical outer wall, and a substantially cylindrical inner wall together defining a substantially ring-shaped interior chamber containing a filtration membrane, the inner wall defining a substantially cylindrical opening in the housing of the arterial filter, the housing having a blood inlet connected to the interior chamber on a first side of the filtration membrane and a blood outlet connected to the interior chamber on a second side of the filtration membrane, to define a blood flow path through the filtration membrane, the blood inlet of the arterial filter being connected to the blood outlet of the oxygenator, the housing of the oxygenator being rigidly connected to the housing of the arterial filter and positioned in the substantially cylindrical opening in the housing of the arterial filter.

In a third aspect, this invention is an integrated device for use in an extracorporeal blood circuit, comprising a housing defining a first portion and a second portion; means for oxygenating blood contained within the first portion of the housing, the oxygenating means including a blood inlet and a blood outlet; and means for filtering oxygenated blood, the filtering means having a blood inlet connected to receive blood from the blood outlet of the oxygenating means and a blood outlet.

In a fourth aspect, this invention is a monolithic device for use in extracorporeal blood circuit, comprising a housing having a blood oxygenator portion and an arterial blood filter portion, the blood oxygenator portion containing a gas exchange membrane and having a blood inlet and a blood outlet defining a blood flow path along a first side of the gas exchange membrane and having a gas inlet and a gas outlet for defining a gas flow path along a second side of the gas exchange membrane, the arterial blood filter portion containing a filtration membrane and having a blood inlet and a blood outlet defining a blood flow path through the filtration membrane, the blood inlet of the arterial blood filter portion being connected to receive blood from the blood outlet of the blood oxygenator portion.

In a fifth aspect, this invention is an arterial blood filter comprising a housing having a top surface, a bottom surface, a substantially cylindrical outer wall and a substantially cylindrical inner wall together defining a substantially ring-shaped interior chamber, the inner wall defining a substantially cylindrical opening from the top surface to the bottom surface of the housing; a filtration membrane contained within the ring-shaped interior chamber; a blood inlet; and a blood outlet, the blood inlet and blood outlet being positioned on the housing to define a blood flow path through the housing across the filtration membrane.

BRIEF DESCRIPTION OF THE DRAWINGS

Further characteristics and advantages will become apparent from the description of a preferred but not exclusive embodiment of the invention, illustrated only by way of non-limiting example in the accompanying drawings, wherein.

BRIEF DESCRIPTION OF THE PREFERRED EMBODIMENTS

With reference to the FIGS. 1 to 8, the numeral 1 generally designates the device, which comprises a first structure, generally designated by the reference numeral 2, and a second structure, generally designated by the reference numeral 3, which are monolithically connected.

Structure 2, which constitutes the actual oxygenator, comprises cylindrical walls 4 and 5, which are suitable to define a portion of space 6 comprising an oxygenation chamber that contains in a known manner hollow fibers or capillaries made of microporous membrane which convey oxygen through the lumens of the fibers from gas inlet port 25 to gas outlet port 27. The structure of the oxygenator is similar to that disclosed in commonly assigned U.S. Pat. No. 5,817,278 (Fini et al.), which is incorporated by reference herein in its entirety. Contained within the central portion of the cylindrical oxygenator is a heat exchanger, also known, which is generally designated by reference numeral 7. The inlet to the heat exchanger includes intake connector 8 which is suitable to be connected to the venous line of an extracorporeal circuit.

Blood enters exchanger 7 through inlet 8, flows through it, and reaches the outlet 9 of the heat exchanger. The outlet of the heat exchanger includes connector 9 that leads into a portion of space 6. Blood entering space 6 through connector 9 wets from the outside the capillaries contained therein until the blood arrives, after being oxygenated, at the outlet of the oxygenator. Delivery connector 10 provides a fluid path from the outlet of the oxygenator to the inlet of structure 3. Connector 10 is located in a higher position in order to ensure the elimination of air bubbles, all as shown by the arrows in the figures.

The structure generally designated by reference numeral 3 is monolithically connected to first structure 2 described above and acts as an arterial filter. Structure 3 is annular and comprises housing 30 which defines an internal portion of space which comprises blood distribution chamber 11, intermediate region 12 which comprises filtration means 28, and blood collection chamber 13.

Figure 1:
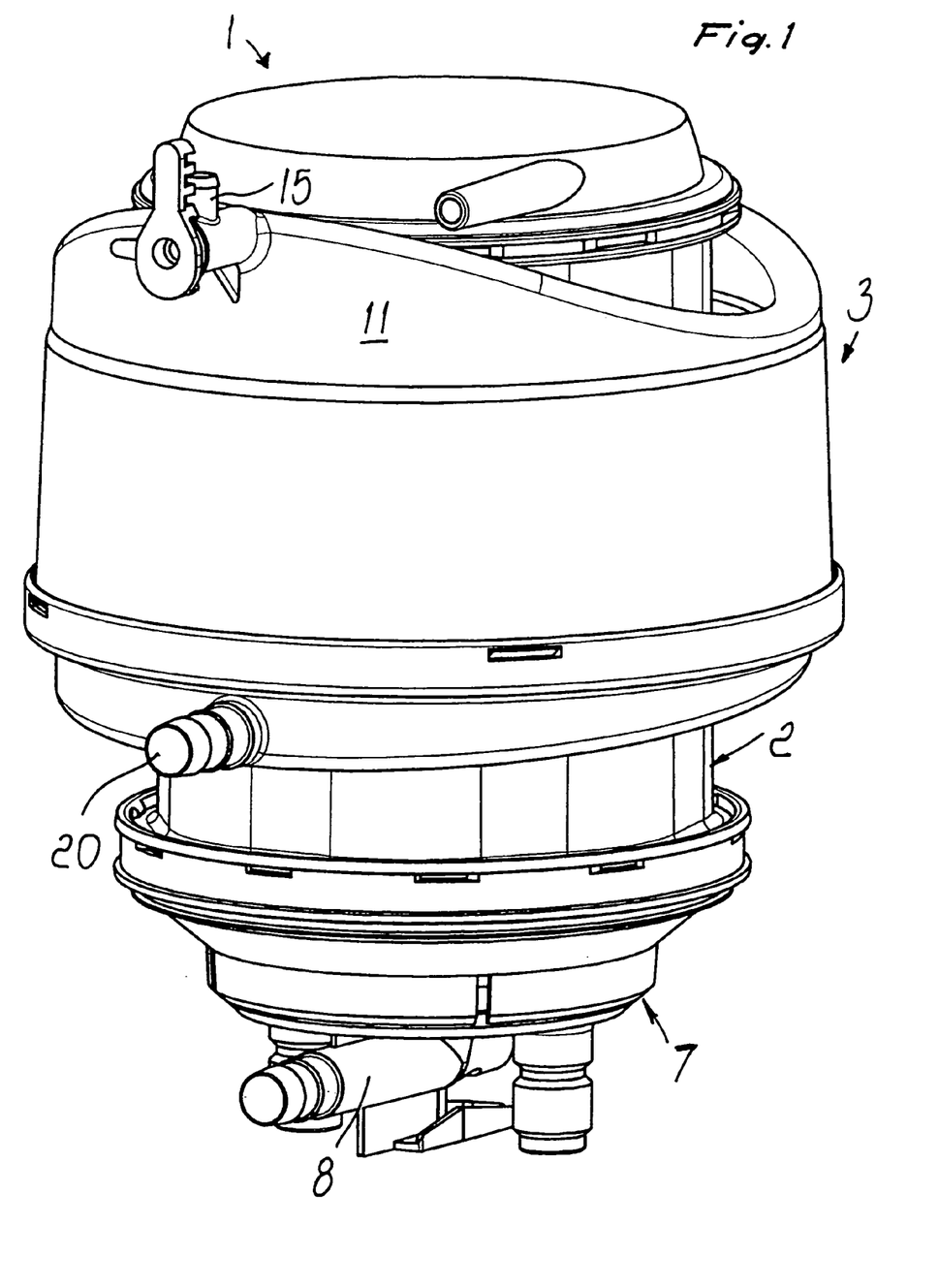
FIG. 1 is a perspective view of the blood oxygenation device of this invention.
Figure 2:
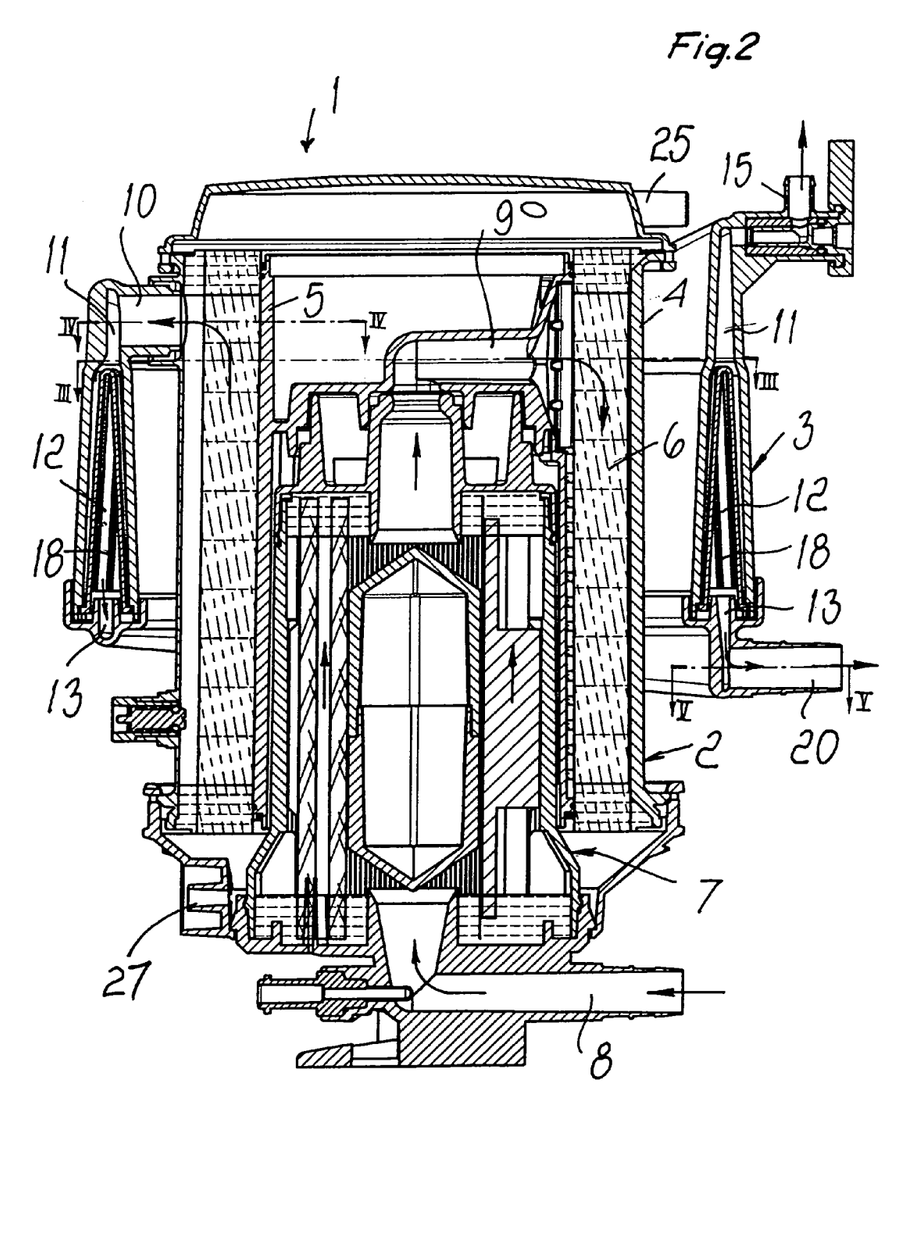
FIG. 2 is a sectional view, along a longitudinal plane, of the device shown in FIG. 1.
Figure 3:
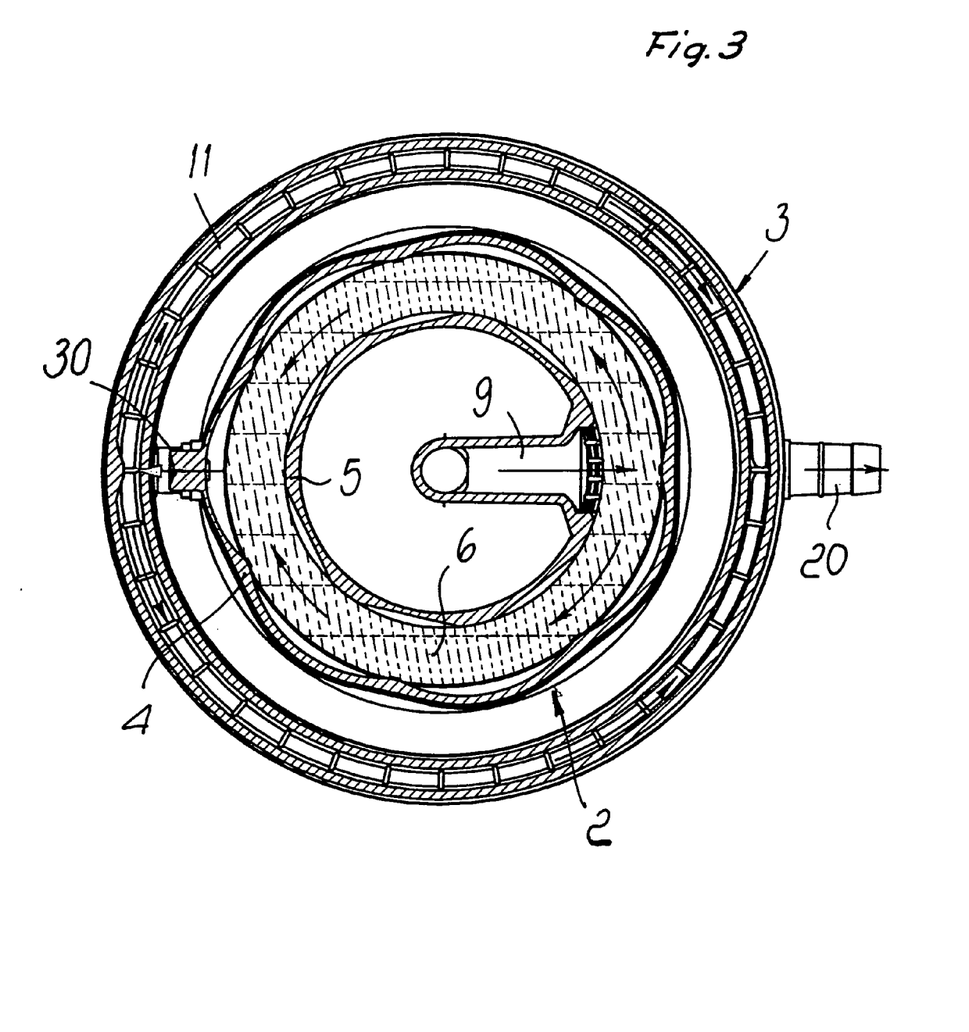
FIG. 3 is a sectional view, taken along the transverse plane III—III of the device shown in FIG. 2.
Figure 4:
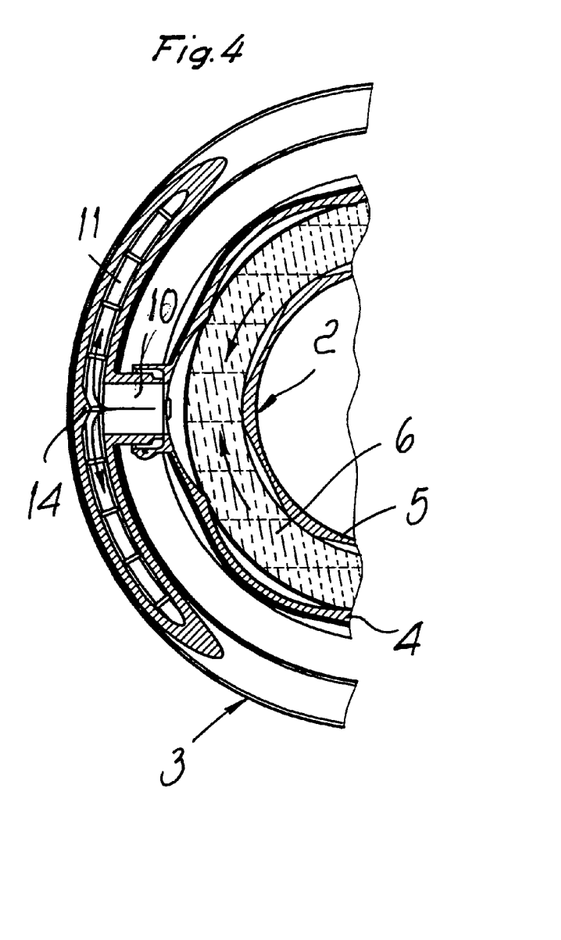
FIGS. 4 and 5 are sectional views, taken respectively along the plane IV—IV and along the plane V—V of FIG. 2.
Figure 5:
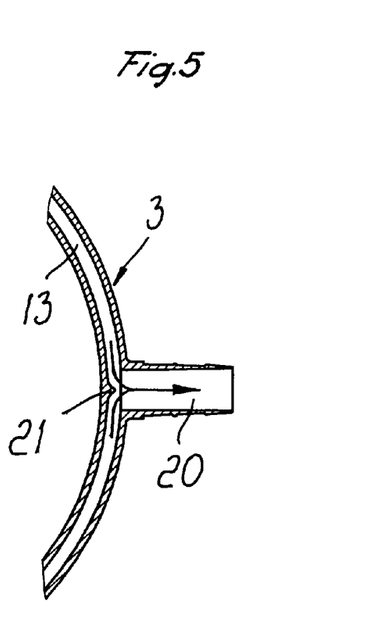

As shown in FIG. 4, blood distribution chamber 11 is connected to connector 10 for receiving the outflow of the blood from the oxygenator at a region which is provided with crest 14 which is suitable to split the blood into two half-ring-shaped flow paths which lie on opposite sides with respect to connector 10 and extend to the diametrically opposite region, where air vent 15 is provided.

Figure 8:
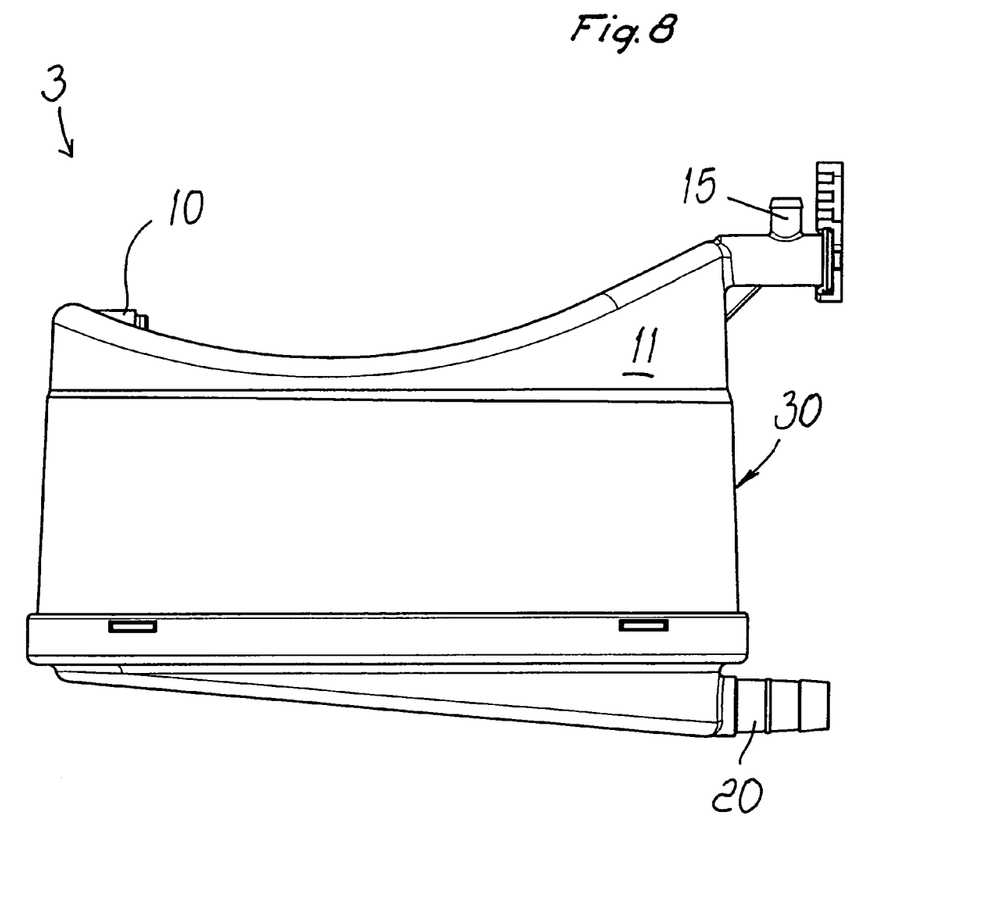
FIG. 8 is a side view of the arterial filter.

The flow path followed by each half-ring, as shown in the figures, is through the internal space defined by the housing of the arterial filter. The housing has a constant base dimension and a height which decreases from the region adjacent connector 10, and then increases to a maximum value at air vent 15 as best seen in FIG. 8. The cross-sectional area of the internal space defining the blood flow passage is a function of the height of the housing. Consequently, the cross-sectional area of the internal space or blood flow passage at the inlet of the arterial filter is greater than that of the cross-sectional area at locations where the height is less than at the inlet.

This leads to a situation in which the blood, after slowing down at the inlet of structure 3, with an initial separation of any air bubbles contained therein, accelerates along a certain extent, facilitating the transport of the bubbles, which thus do not risk remaining trapped in the blood, and finally slows down again proximate to the vent, assuming the best conditions for the final separation of the bubbles, which leave through the vent.

If the amount of air bubbles present in the blood is modest, the described fluid-dynamics treatment can be sufficient to eliminate them completely. If instead the amount is considerable, the filtration membrane completes their elimination from the blood before the blood returns to the patient.

Figure 6:
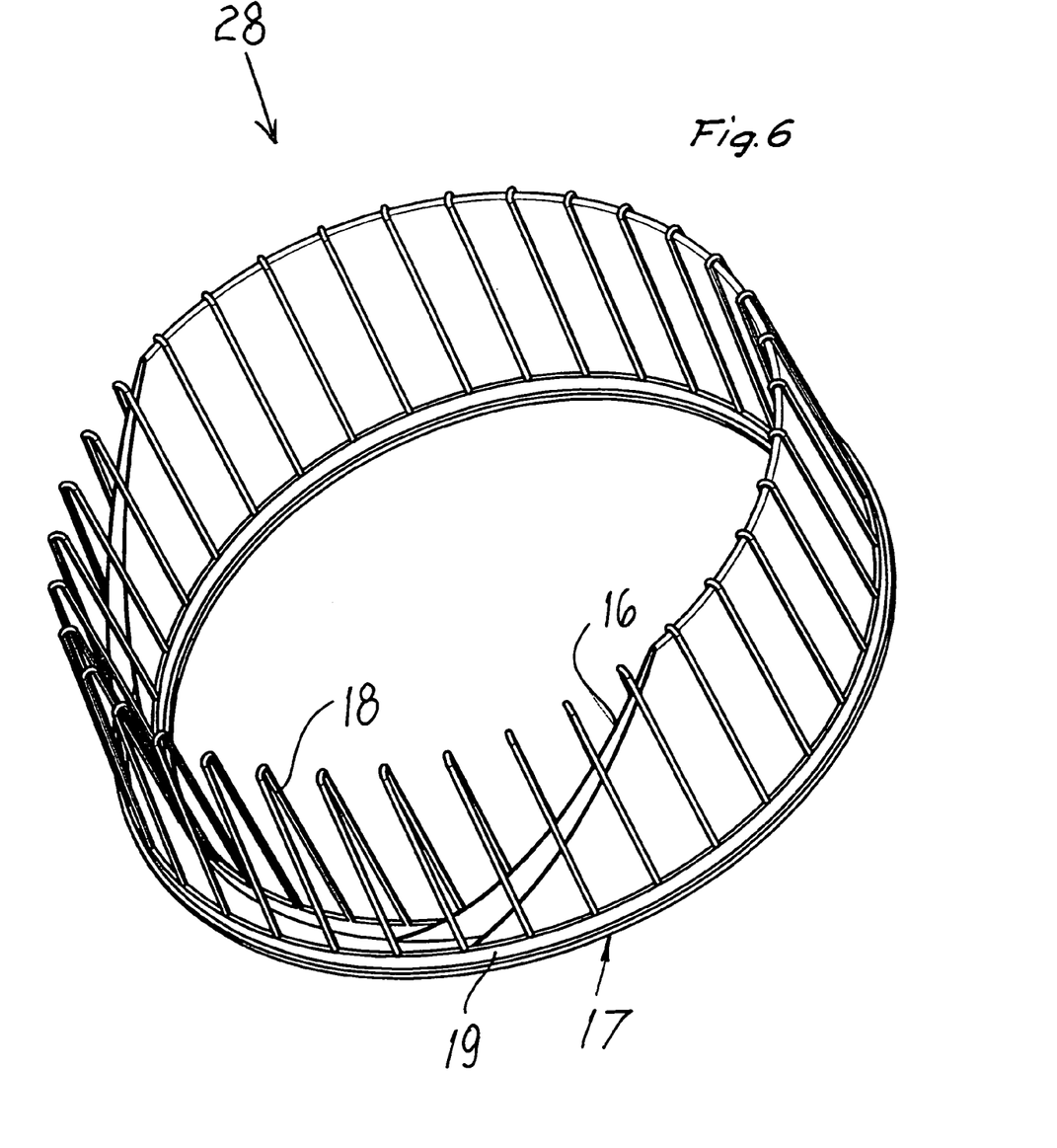
FIG. 6 is a perspective view of the filtration means with a portion of filtration membrane cut away.
Figure 7:
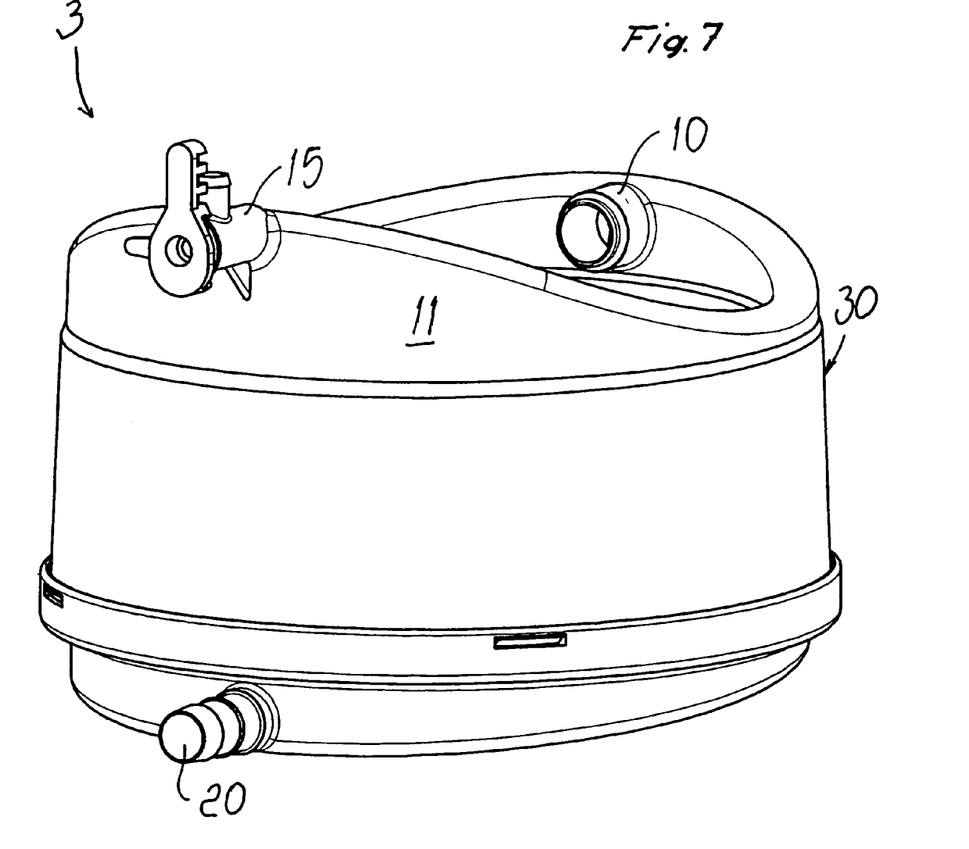
FIG. 7 is a perspective view of the arterial filter.

Blood filtration means 28 contained in region 12 comprises filtration membrane 16, which is supported by annular frame 17. As best seen in FIG. 6, where a portion of the filtration membrane in removed, annular frame 17 comprises wire-like radial U-shaped bridges, such as 18, which extend monolithically from footing 19, which has a constant width. Blood flowing in either half-ring flow path must pass through filtration membrane 16 in order to flow from the inlet to the outlet of the arterial filter.

The blood, after passing through filtration means 28, passes into lower collection chamber 13, (FIG. 5) which is provided with outlet port 20 which is suitable to be connected to the arterial line of the extracorporeal circuit. The lower collection chamber has a constant width and a height which gradually increases from the inlet side of the arterial filter (at connector 10) to the outlet side of the arterial filter (at outlet port 20), to which the blood flow is directed by crest 21.

The described invention is susceptible of numerous modifications and variations, all of which are within the scope of the inventive concept. Thus, for example, the actual oxygenator, which in the described embodiment replicates the content of U.S. Pat. No. 5,817,278 (Fini et al.), may be of any kind, including oxygenators having microporous hollow fiber bundles of various constructions, flat sheet microporous membranes, semi-permeable membranes, and other configurations and structures as known in the art.

What is claimed is:

1. A device for oxygenating, filtering and controlling the temperature of blood in an extracorporeal circuit comprising a monolithic housing defining first, second and third interior chambers, the first chamber having a substantially cylindrical shape defining a central portion and containing a plurality of microporous hollow fibers and having a blood inlet and a blood outlet connected to the first chamber to define a blood flow path along an exterior of the hollow fibers and having a gas inlet and a gas outlet connected to the first chamber to define a gas flow path through the lumens of the hollow fibers, the second chamber being positioned substantially within the central portion of the first chamber and containing a heat exchange surface and having a blood inlet and a blood outlet connected to the second chamber to define a blood flow path through the second chamber adjacent the heat exchange surface, the blood outlet of the second chamber being connected to the blood inlet of the first chamber, the third chamber containing a filtration membrane and having a blood inlet and a blood outlet connected to the third chamber to define a blood flow path through the filtration membrane, the blood inlet of the third chamber being connected to receive blood from the blood outlet of the first chamber.

2. An integrated device for use in an extracorporeal blood circuit, comprising:

a housing defining a first portion and a second portion, the second portion being substantially ring-shaped and having an inner wall defining a substantially cylindrical opening, the first portion being positioned substantially within the cylindrical opening;

means for oxygenating blood contained within the first portion of the housing, the oxygenating means including a blood inlet and a blood outlet; and means for filtering oxygenated blood contained within the second portion, the filtering means having a blood inlet connected to receive blood from the blood outlet of the oxygenating means, a blood outlet, and a blood distribution chamber having a first cross-sectional area at the blood inlet and a second cross-sectional area at a location radially spaced from the blood inlet, the first cross-sectional area being greater than the second cross-sectional area.

3. A monolithic device for use in an extracorporeal blood circuit, comprising a housing having a blood oxygenator portion, a heat exchanger portion and an arterial blood filter portion, the blood oxygenator portion having a substantially cylindrical shape defining a central opening and containing a gas exchange membrane and having a blood inlet and a blood outlet defining a blood flow path along a first side of the gas exchange membrane and having a gas inlet and a gas outlet for defining a gas flow path along a second side of the gas exchange membrane, the arterial blood filter portion containing a filtration membrane and having a blood inlet and a blood outlet defining a blood flow path through the filtration membrane, the blood inlet of the arterial blood filter portion being connected to receive blood from the blood outlet of the blood oxygenator portion, the heat exchanger portion being contained substantially within the central opening of the oxygenator portion and having a blood inlet and a blood outlet connected to define a blood flow path through the heat exchanger portion, the blood outlet of the heat exchanger portion being connected to the blood inlet of the oxygenator portion.

4. The device of claim 1 wherein the blood inlet connected to the third chamber is positioned above the blood outlet connected to the third chamber to define the blood flow path through the filtration membrane from a top of the third chamber to a bottom of the third chamber.

5. The device of claim 3 wherein the blood inlet and the blood outlet of the heat exchanger are connected to define an upward blood flow path through the heat exchanger portion.

* * * * *